(12) United States Patent
Stahl et al.

(10) Patent No.: US 12,268,898 B2
(45) Date of Patent: *Apr. 8, 2025

(54) SYSTEMS AND METHODS FOR MULTIPLANAR RADIATION TREATMENT

(71) Applicant: SHANGHAI UNITED IMAGING HEALTHCARE CO., LTD., Shanghai (CN)

(72) Inventors: Johannes Stahl, Houston, TX (US); Jonathan Maltz, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/433,361

(22) Filed: Feb. 5, 2024

(65) Prior Publication Data

US 2024/0207646 A1   Jun. 27, 2024

Related U.S. Application Data

(63) Continuation of application No. 18/061,991, filed on Dec. 5, 2022, now Pat. No. 11,896,846, which is a (Continued)

(51) Int. Cl.
*A61N 5/10* (2006.01)

(52) U.S. Cl.
CPC ......... *A61N 5/1045* (2013.01); *A61N 5/1036* (2013.01); *A61N 5/1049* (2013.01); (Continued)

(58) Field of Classification Search
CPC .. A61N 5/1031; A61N 5/1036; A61N 5/1039; A61N 5/1045; A61N 5/1049; A61N 5/1077

See application file for complete search history.

(56) References Cited

U.S. PATENT DOCUMENTS 10,967,200 B2    4/2021   Stahl et al.
11,517,770 B2   12/2022   Stahl et al.
(Continued)

FOREIGN PATENT DOCUMENTS

| CN | 101120871 A | 2/2008 |
| EP | 2837406 A1 | 2/2015 |
| WO | 2019127443 A1 | 7/2019 |

OTHER PUBLICATIONS

International Search Report in PCT/CN2018/071685 mailed on Sep. 14, 2018, 5 pages.
(Continued)

*Primary Examiner* — Chih-Cheng Kao
(74) *Attorney, Agent, or Firm* — METIS IP LLC

(57) ABSTRACT

A method for delivering radiation treatment may include defining a preliminary trajectory including a plurality of control points. Each control point may be associated with position parameters of a gantry and a couch. The method may also include generating a treatment plan based on the preliminary trajectory by optimizing an intensity and position parameters of a collimator and MLC leaves for each control point. The method may also include decomposing the treatment plan into a delivery trajectory including the plurality of control points. Each of the plurality of control points may be further associated with the optimized intensity, the optimized position parameters of the collimator and the MLC leaves, an output rate, and a motion parameter of each of the gantry, the couch, the collimator, and the MLC leaves. The method may further include instructing a radiation delivery device to deliver the treatment plan according to the delivery trajectory.

20 Claims, 11 Drawing Sheets

Related U.S. Application Data continuation of application No. 17/218,093, filed on Mar. 30, 2021, now Pat. No. 11,517,770, which is a continuation of application No. 16/220,239, filed on Dec. 14, 2018, now Pat. No. 10,967,200, which is a continuation of application No. PCT/CN2018/071685, filed on Jan. 6, 2018.

(52) U.S. Cl.
CPC .... *A61N 5/1031* (2013.01); *A61N 2005/1032* (2013.01); *A61N 2005/1035* (2013.01); *A61N 5/1039* (2013.01); *A61N 2005/1041* (2013.01); *A61N 5/1077* (2013.01)

(56) References Cited

U.S. PATENT DOCUMENTS

| | | | | |
|---|---|---|---|---|
| 11,896,846 B2* | 2/2024 | Stahl | ............... | A61N 5/1049 |
| 2002/0006182 A1* | 1/2002 | Kim | ............... | A61N 5/1084 |
| | | | | 378/65 |
| 2005/0254622 A1 | 11/2005 | Llacer | | |
| 2007/0041500 A1 | 2/2007 | Olivera et al. | | |
| 2008/0226030 A1 | 9/2008 | Otto | | |
| 2010/0054409 A1 | 3/2010 | Bose et al. | | |
| 2010/0054410 A1 | 3/2010 | Nord et al. | | |
| 2011/0091014 A1 | 4/2011 | Siljamaki et al. | | |
| 2011/0122997 A1 | 5/2011 | Lu et al. | | |
| 2013/0072742 A1 | 3/2013 | Nord et al. | | |
| 2013/0142310 A1 | 6/2013 | Fahimian et al. | | |
| 2015/0190658 A1 | 7/2015 | Yu | | |
| 2016/0059040 A1 | 3/2016 | Paliwal et al. | | |
| 2019/0046132 A1 | 2/2019 | Xu | | |
| 2019/0051398 A1 | 2/2019 | Zankowski et al. | | |
| 2019/0060669 A1 | 2/2019 | Stahl et al. | | |

OTHER PUBLICATIONS

Written Opinion in PCT/CN2018/071685 mailed on Sep. 14, 2018, 4 pages.
First Office Action in Chinese Application No. 201880002703.4 mailed on May 12, 2020, 20 pages.
The Second Office Action in Chinese Application No. 201880002703.4 mailed on Feb. 8, 2021, 25 pages.

* cited by examiner

300

600

```
┌─────────────────────────────────────────────────┐
│ Defining a preliminary trajectory including a   │
│ plurality of control points, each of the        │──── 602
│ plurality of control points being associated    │
│ with a position parameter of a gantry and a     │
│ position parameter of a couch                   │
└─────────────────────────────────────────────────┘
                        ↓
┌─────────────────────────────────────────────────┐
│ Generating a treatment plan based on the        │
│ preliminary trajectory by optimizing an         │──── 604
│ intensity, a position parameter of a collimator,│
│ and a position parameter of MLC leaves for each │
│ control point                                   │
└─────────────────────────────────────────────────┘
                        ↓
┌─────────────────────────────────────────────────┐
│ Decomposing the treatment plan into a target    │
│ trajectory including the plurality of control   │
│ points, each of the plurality of control points │
│ being further associated with the optimized     │──── 606
│ intensity, the optimized position parameter of  │
│ the collimator, the optimized position parameter│
│ of the MLC leaves, and a motion parameter of    │
│ each of the gantry, the couch, the collimator,  │
│ and MLC leaves                                  │
└─────────────────────────────────────────────────┘
                        ↓
┌─────────────────────────────────────────────────┐
│ Instructing a radiation delivery device to      │──── 608
│ deliver the treatment plan to the subject       │
└─────────────────────────────────────────────────┘
```

FIG. 6

SYSTEMS AND METHODS FOR MULTIPLANAR RADIATION TREATMENT

CROSS-REFERENCE TO RELATED APPLICATION

This application is a continuation application of U.S. application Ser. No. 18/061,991, field on Dec. 5, 2022, which is a continuation application of U.S. application Ser. No. 17/218,093 (now U.S. Pat. No. 11,517,770), field on Mar. 30, 2021, which is a continuation application of U.S. application Ser. No. 16/220,239 (now U.S. Pat. No. 10,967,200), field on Dec. 14, 2018, which is a Continuation of International Application No. PCT/CN2018/071685, filed on Jan. 6, 2018, the entire content of which is hereby incorporated by reference.

TECHNICAL FIELD

The present disclosure generally relates to radiation treatment (RT), and more particularly, relates to systems and methods for multiplanar RT.

BACKGROUND

Radiation treatment has been widely used for clinical treatment of cancers and other conditions. A fundamental goal of the radiation treatment is to kill cells (usually tumor cells), suppress inflammation, suppress the immune system, or prevent tumor recurrence by using high-energy radiation beams such as X-rays, gamma rays, alpha rays, beta rays, etc. One of the most challenging problems in the radiation treatment is to locate a region of interest (ROI) precisely for receiving the radiation treatment so as to reduce unnecessary radiation toward the normal organs or tissues surrounding the ROI. The control of radiation beams may be more flexible to avoid critical organs if the gantry and the couch move synchronously during delivery of the radiation treatment, since the radiation source may traverse multiple planes. Therefore, it is desirable to develop systems and methods for multiplanar RT.

SUMMARY

According to an aspect of the present disclosure, a system for delivering radiation treatment to a subject is provided. The system may include a storage device storing a set of instructions and at least one processor configured to communicate with the storage device. When executing the set of instructions, the at least one processor may be configured to direct the system to define a preliminary trajectory. The preliminary trajectory may include a plurality of control points. Each of the plurality of control points may be associated with a position parameter of a gantry and a position parameter of a couch. The at least one processor may also direct the system to generate a treatment plan based on the preliminary trajectory by optimizing an intensity, a position parameter of a collimator, and a position parameter of multi-leaf collimator (MLC) leaves for each control point. The at least one processor may further direct the system to decompose the treatment plan into a delivery trajectory. The delivery trajectory may include the plurality of control points. Each of the plurality of control points may be further associated with the optimized intensity, the optimized position parameter of the collimator, the optimized position parameter of the MLC leaves, an output rate, and a motion parameter of each of the gantry, the couch, the collimator, and the MLC leaves. The at least one processor may also direct the system to instruct a radiation delivery device to deliver the treatment plan to the subject according to the delivery trajectory.

In some embodiments, the optimization of the intensity, the position parameter of the collimator, and the position parameter of the MLC leaves may be performed using at least one of a direct aperture optimization (DAO) technique or a fluence map optimization (FMO) technique.

In some embodiments, the at least one processor may be further configured to direct the system to perform a collision check on at least one of the preliminary trajectory or the delivery trajectory to avoid collision between the gantry and the subject or the couch during the delivering of the treatment plan to the subject.

In some embodiments, to define the preliminary trajectory, the at least one processor may be further configured to direct the system to obtain a plurality of predetermined trajectories with respect to an organ to be treated. The at least one processor may also be configured to direct the system to select the preliminary trajectory from the plurality of predetermined trajectories.

In some embodiments, the preliminary trajectory may be selected to minimize radiations to at least one of a heart, a chest cavity, a hippocampus, a temporal brain lobe, or a contralateral breast of the subject.

In some embodiments, the plurality of predetermined trajectories may be generated based on historical patient treatment data using a machine learning technique.

In some embodiments, the organ to be treated may be at least one of a breast or a brain.

In some embodiments, the organ to be treated may be a breast and the subject may be treated in a prone position.

In some embodiments, the motion parameter of the couch may be associated with at least one of a translation motion, a pitch motion, or a roll motion. A motion of the couch may be synchronous to the delivering of the treatment plan according to the delivery trajectory.

In some embodiments, the position parameter of the collimator may include a collimator angle. The optimization of the collimator angle may be performed within a range determined based on at least one of clinical application or an organ to be treated.

According to another aspect of the present disclosure, a method for delivering radiation treatment to a subject is provided. The method may be implemented on at least one processor and a storage. The method may include defining a preliminary trajectory including a plurality of control points. Each of the plurality of control points may be associated with a position parameter of a gantry and a position parameter of a couch. The method may also include generating a treatment plan based on the preliminary trajectory by optimizing an intensity, a position parameter of a collimator, and a position parameter of MLC leaves for each control point. The method may also include decomposing the treatment plan into a delivery trajectory. The delivery trajectory may include the plurality of control points. Each of the plurality of control points may be further associated with the optimized intensity, the optimized position parameter of the collimator, the optimized position parameter of the MLC leaves, an output rate, and a motion parameter of each of the gantry, the couch, the collimator, and the MLC leaves. The method may further include instructing a radiation delivery device to deliver the treatment plan to the subject according to the delivery trajectory.

According to yet another aspect of the present disclosure, a non-transitory computer readable medium is provided. The non-transitory computer readable medium may include executable instructions. When executed by at least one processor, the executable instructions may cause the at least one processor to effectuate a method for delivering radiation treatment to a subject. The method may include defining a preliminary trajectory. The preliminary trajectory may include a plurality of control points. Each of the plurality of control points may be associated with a position parameter of a gantry and a position parameter of a couch. The method may also include generating a treatment plan based on the preliminary trajectory by optimizing an intensity, a position parameter of a collimator, and a position parameter of MLC leaves for each control point. The method may also include decomposing the treatment plan into a delivery trajectory. The delivery trajectory may include the plurality of control points. Each of the plurality of control points may be further associated with the optimized intensity, the optimized position parameter of the collimator, the optimized position parameter of the MLC leaves, an output rate, and a motion parameter of each of the gantry, the couch, the collimator, and the MLC leaves. The method may further include instructing a radiation delivery device to deliver the treatment plan to the subject according to the delivery trajectory.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for delivering a treatment plan according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" May be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
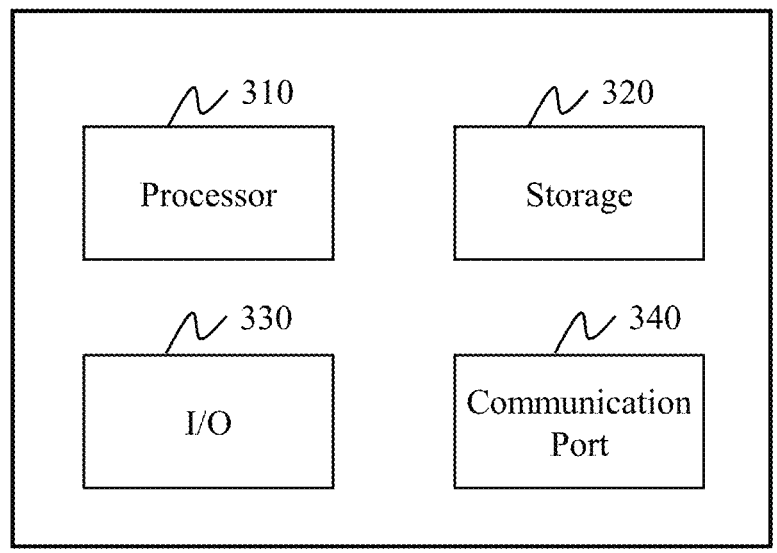
FIG. 3 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure generally relates to radiation treatment. Radiation beams used for the radiation treatment may include particle beams (e.g., a neutron beam, a proton beam, an electron beam, etc.), photon beams (e.g., an X-ray, a γ-ray), or the like, or a combination thereof. Provided herein are mechanisms (which can include methods, systems, computer-readable medium, etc.) for mutiplanar RT. For example, the systems and/or methods provided in the present disclosure may define a preliminary trajectory including a plurality of control points. Each control point may be associated with a position parameter of a gantry and a position parameter of a couch. A treatment plan may be generated based on the preliminary trajectory and an optimization of an intensity, a position parameter of a collimator, and a position parameter of MLC leaves. Then the treatment plan may be decomposed into a multiplanar delivery trajectory including the plurality of control points. Each control point may be further associated with the optimized intensity, the optimized collimator position parameter, the optimized MLC leaf position, and motion parameters of the multiple components of the radiation delivery device. Each control point could be further associated with an output rate which could be predetermined or as a constraint during optimization. An instruction may be sent to direct the radiation delivery device to synchronously control the motions of the multiple components and deliver the treatment plan to the subject. During the treatment delivery, according to the delivery trajectory, the multiple components of the radiation delivery device may simultaneously move with independently controlled motion parameters so that the radiation source may traverse multiple planes to better avoid the healthy organs.

Figure 1:
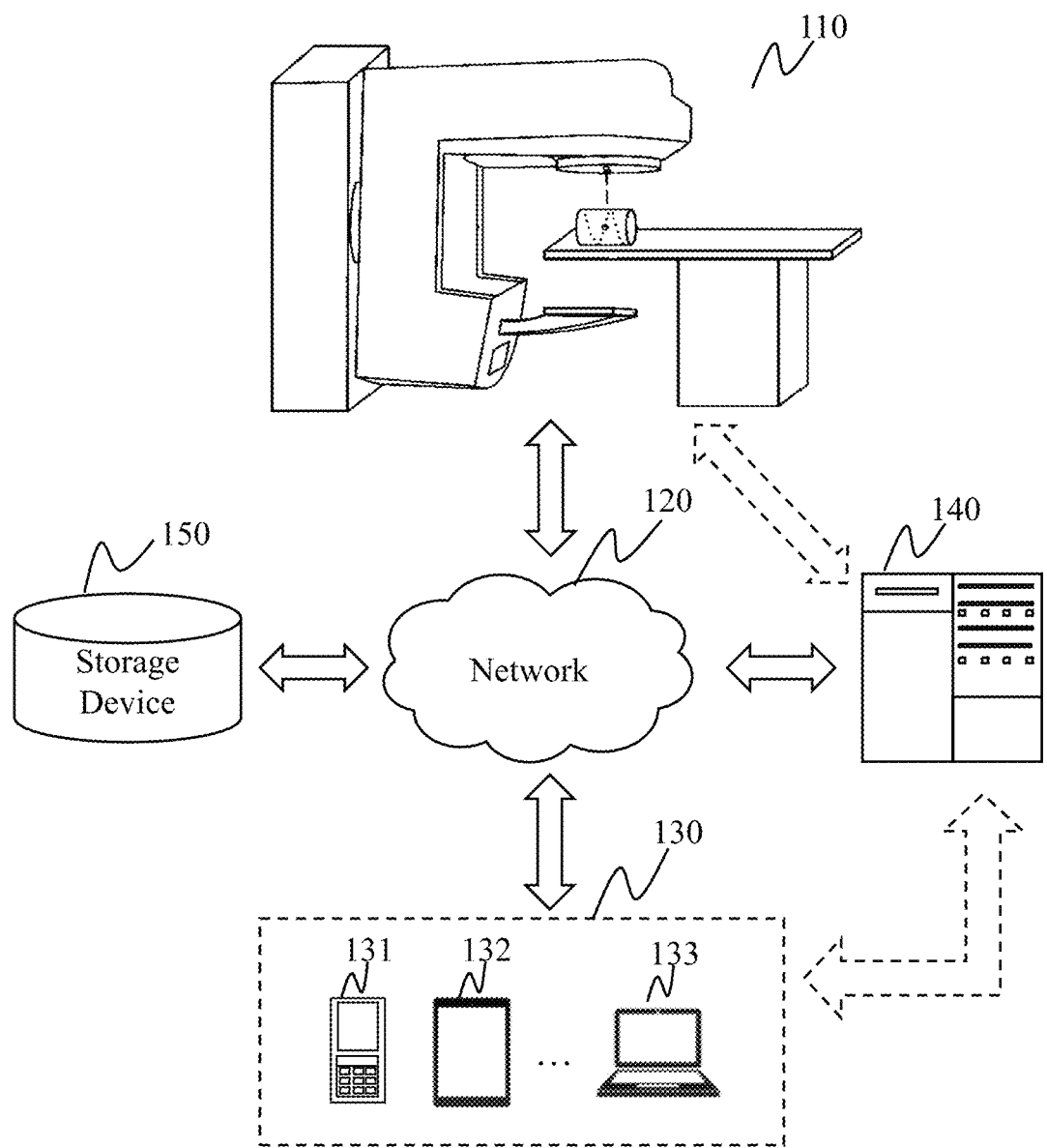
FIG. 1 is a schematic diagram illustrating an exemplary RT system according to some embodiments of the present disclosure.

FIG. 1 is a schematic diagram illustrating an exemplary RT system 100 according to some embodiments of the present disclosure. As shown, the RT system 100 may include a radiation delivery device 110, a network 120, one or more terminals 130, a processing engine 140, and a storage device 150. In some embodiments, the radiation delivery device 110, the terminal(s) 130, the processing engine 140, and/or the storage device 150 may be connected to and/or communicate with each other via a wireless connection (e.g., the network 120), a wired connection, or a combination thereof. The connection between the components of the RT system 100 may be variable. Merely by way of example, the radiation delivery device 110 may be connected to the processing engine 140 through the network 120, as illustrated in FIG. 1. As another example, the radiation delivery device 110 may be connected to the processing engine 140 directly. As a further example, the storage device 150 may be connected to the processing engine 140 through the network 120, as illustrated in FIG. 1, or connected to the processing engine 140 directly. As still a further example, a terminal 130 may be connected to the processing engine 140 through the network 120, as illustrated in FIG. 1, or connected to the processing engine 140 directly.

The radiation delivery device 110 may deliver a treatment plan to a subject (e.g., a patient) on a couch of the radiation delivery device 110. In some embodiments, the radiation delivery device 110 may be a multi-modality (e.g., two-modality) apparatus to acquire a medical image and perform radio therapy. The medical image may be a Computed Tomography (CT) image, a Magnetic Resonance (MR) image, an ultrasonic image, a four-dimensional (4D) image, a three-dimensional (3D) image, a two-dimensional (2D) image, a diagnostic image, and a non-diagnostic image, or the like, or a combination thereof. The radiation delivery device 110 may include one or more imaging devices and/or treatment devices. For example, a CT device, a Cone beam CT, a Positron Emission Tomography (PET), a Volume CT, an MRI device, an RT device, or the like, or a combination thereof. In some embodiments, the imaging device(s) may acquire an image of the subject prior to an RT treatment, during an RT treatment and/or after an RT treatment. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or ROI, such as an esophagus, a trachea, a bronchus, a stomach, a gallbladder, a small intestine, a colon, a bladder, a ureter, a uterus, a fallopian tube, etc.

The network 120 may include any suitable network that can facilitate exchange of information and/or data for the RT system 100. In some embodiments, one or more components of the RT system 100 (e.g., the radiation delivery device 110, the processing engine 140, the storage device 150, the terminal(s) 130) may communicate information and/or data with one or more other components of the RT system 100 via the network 120. For example, the processing engine 140 may obtain image data from the radiation delivery device 110 via the network 120. As another example, the processing engine 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

The terminal(s) 130 may be connected to and/or communicate with the radiation delivery device 110, the processing engine 140, and/or the storage device 150. For example, the terminal(s) 130 may obtain a processed image from the processing engine 140. As another example, the terminal(s) 130 may obtain image data acquired via the radiation delivery device 110 and transmit the image data to the processing engine 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing engine 140.

The processing engine 140 may process data and/or information obtained from the radiation delivery device 110, the storage device 150, the terminal(s) 130, or other components of the RT system 100. For example, the processing engine 140 may reconstruct an image based on projection data generated by the radiation delivery device 110. As another example, the processing engine 140 may generate an RT treatment plan by optimizing relevant parameters. In some embodiments, the processing engine 140 may be a single server or a server group. The server group may be centralized or distributed. In some embodiments, the processing engine 140 may be local to or remote from the RT system 100. For example, the processing engine 140 may access information and/or data from the radiation delivery device 110, the storage device 150, and/or the terminal(s) 130 via the network 120. As another example, the processing engine 140 may be directly connected to the radiation delivery device 110, the terminal(s) 130, and/or the storage device 150 to access information and/or data. In some embodiments, the processing engine 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 140 may be implemented by a computing device 300 having one or more components as described in connection with FIG. 3.

The storage device 150 may store data, instructions, and/or any other information. In some embodiments, the storage device 150 may store data obtained from the radiation delivery device 110, the terminal(s) 130, and/or the processing engine 140. In some embodiments, the storage device 150 may store data and/or instructions that the processing engine 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the RT system 100 (e.g., the processing engine 140, the terminal(s) 130). One or more components of the RT system 100 may access the data or instructions stored in the storage device 150 via the network 120. In some embodiments, the storage device 150 may be part of the processing engine 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as, public cloud, private cloud, community, and hybrid clouds, etc. However, those variations and modifications do not depart the scope of the present disclosure.

Figure 2:
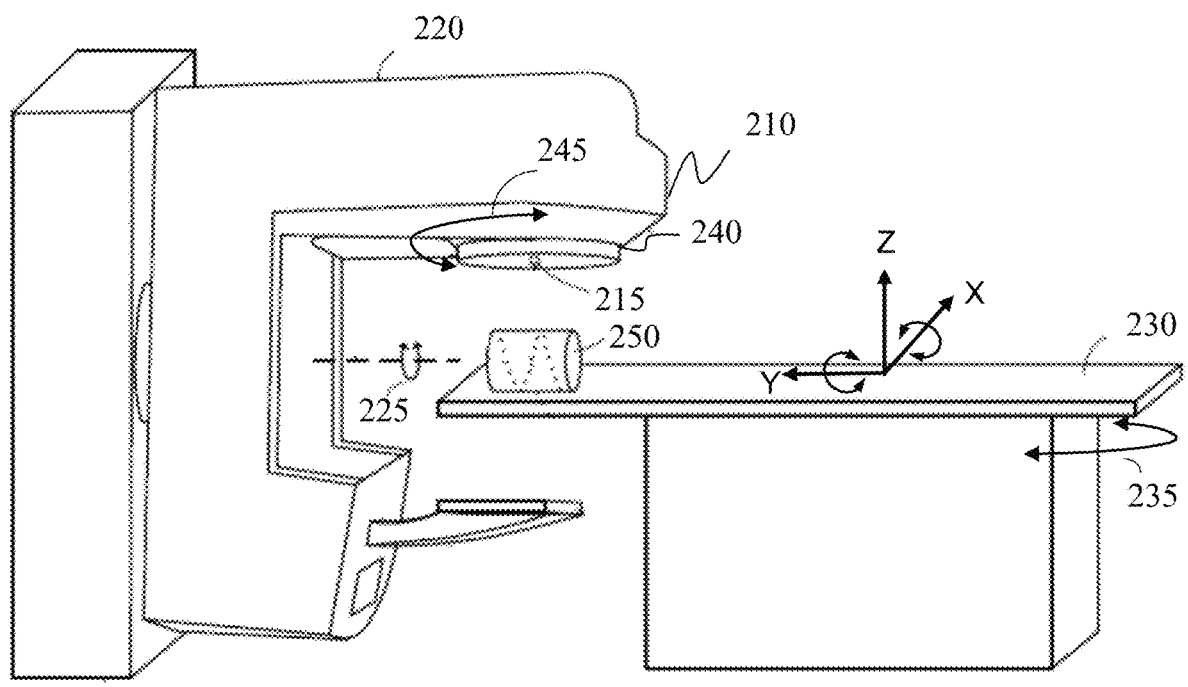
FIG. 2 is a schematic diagram illustrating an exemplary radiation delivery device according to some embodiments of the present disclosure.

FIG. 2 is a schematic diagram illustrating an exemplary radiation delivery device 110 according to some embodiments of the present disclosure. The radiation delivery device 110 may be configured to deliver a treatment plan to a subject 250.

The radiation delivery device 110 may include a treatment head 210, a gantry 220, a couch 230, and a collimator 240. The subject 250 may receive a scanning and/or a radiation treatment in a prone position on the couch 230. The treatment head 210 may include a radiation source 215 that may emit radiation beams toward the subject 250. The radiation beams may include particle beams (e.g., a neutron beam, a proton beam, an electron beam, etc.), photon beams (e.g., an X-ray, a γ-ray, etc.), or the like, or a combination thereof.

One or more components of the radiation delivery device 110 may move in a coordinated manner during the radiation delivery to precisely target the radiation beams to an ROI of the subject 250. The ROI may refer to a region of the subject 250 that needs to be irradiated. For example, the ROI may include malignant tissue (e.g., a tumor, or a cancer-ridden organ) and/or other tissues (e.g., a tissue surrounding the malignant tissue). As another example, the ROI may include an organ not affected by cancer. A physical movement of the subject 250 may cause position deviations of the ROI and cause the radiation beams to hit normal organs or tissues. Thus, in some embodiments, additional components may be used to prevent the physical movement of the subject 250 during the treatment delivery. For example, when the treatment plan is delivered to a breast, the breast portion of the subject 250 may be held stationary by using a suction cup and/or a compression device.

The treatment head 210 may be incorporated in the gantry 220 and move with the gantry 220. The gantry 220 may rotate around the subject 250 in a clockwise direction or an anticlockwise direction as illustrated by an arrow 225 in FIG. 2.

The couch 230 may support the subject 250 and dynamically move during the radiation delivery through translations, rotations, rolls, and/or pitches in a coordinated manner with the motion of other components, such as the gantry 220 and the collimator 240. For illustration purposes, a reference coordinate system as shown in FIG. 2 is introduced. The reference coordinate system may include an X-axis, a Y-axis, and a Z-axis. The X-axis, Y-axis, and Z-axis may be parallel to the lateral, longitudinal, and vertical directions of the couch 230 respectively. The couch 230 may translate along the X, Y, and/or Z directions, roll about the Y direction, and/or pitch about the X direction. The "direction" used herein means parallel to but not necessarily coincident with an axis. Additionally or alternatively, the couch 230 may rotate about any given point in space as indicated by an arrow 235.

The collimator 240 may be configured to shape the radiation beams to conform to the ROI. As used herein, "to conform to the ROI" May refer to accommodating a contour of the ROI to be treated such that the radiation beams may target the ROI while minimizing the radiations to the surrounding normal organs or tissues. The collimator 240 may rotate as indicated by an arrow 245 such that the radiation beams may be modulated to conform to the ROI in a more flexible manner. In some embodiments, the collimator 240 may include an MLC. The MLC may include a plurality of leaves each of which may moves in the path of a radiation beam in order to block it.

Simultaneous modulations of a plurality of components of the radiation delivery device 110 may enable the radiation source 215 to traverse multiple planes with respect to the ROI. Accordingly, the radiation beams may have better dose conformality to the ROI without affecting the healthy organs or tissues surrounding the ROI.

It should be noted that the exemplary radiation delivery device 110 illustrated in FIG. 2 and the above descriptions thereof are merely provided for the purposes of illustration, and not intended to limit the scope of the present disclosure. For persons having ordinary skills in the art, multiple variations or modifications may be made under the teachings of the present disclosure. For example, the couch 230 may move in various directions according to the clinical requirements. As another example, the radiation delivery device 110 may include a control system to modulate the various components at the same time. Merely by way of example, the control system may simultaneously move the gantry 220, the couch 230, the collimator 240, and the MLC leaves, and also modulate the dose delivered to the subject 250 during treatment. However, those variations and modifications do not depart from the scope of the present disclosure.

FIG. 3 is a schematic diagram illustrating exemplary hardware and/or software components of an exemplary computing device 300 on which the processing engine 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 310 may process data of the radiation delivery device 110, the terminals 130, the storage device 150, and/or any other component of the RT system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operation s A and B).

The storage 320 may store data/information obtained from the radiation delivery device 110, the terminals 130, the storage device 150, and/or any other component of the RT system 100. In some embodiments, the storage 320 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing engine 140 for generating a treatment plan for a subject (e.g., an ROI of a patient).

The I/O 330 may input and/or output signals, data, information, etc. In some embodiments, the I/O 330 may enable a user interaction with the processing engine 140. In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 120) to facilitate data communications. The communication port 340 may establish connections between the processing engine 140 and the radiation delivery device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
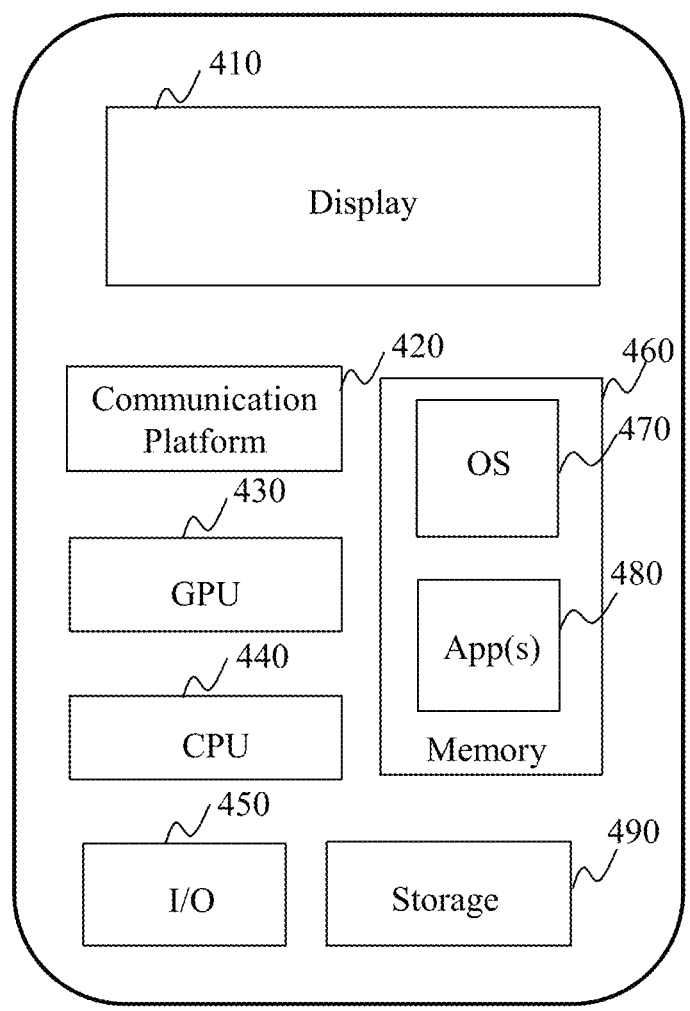
FIG. 4 is a schematic diagram illustrating exemplary hardware and/or software components of an exemplary user terminal according to some embodiments of the present disclosure.

FIG. 4 is a schematic diagram illustrating exemplary hardware and/or software components of an exemplary mobile device 400 on which the terminals 130 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving information and/or data from the processing engine 140. User interactions with the information stream may be achieved via the I/O 450 and provided to the processing engine 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
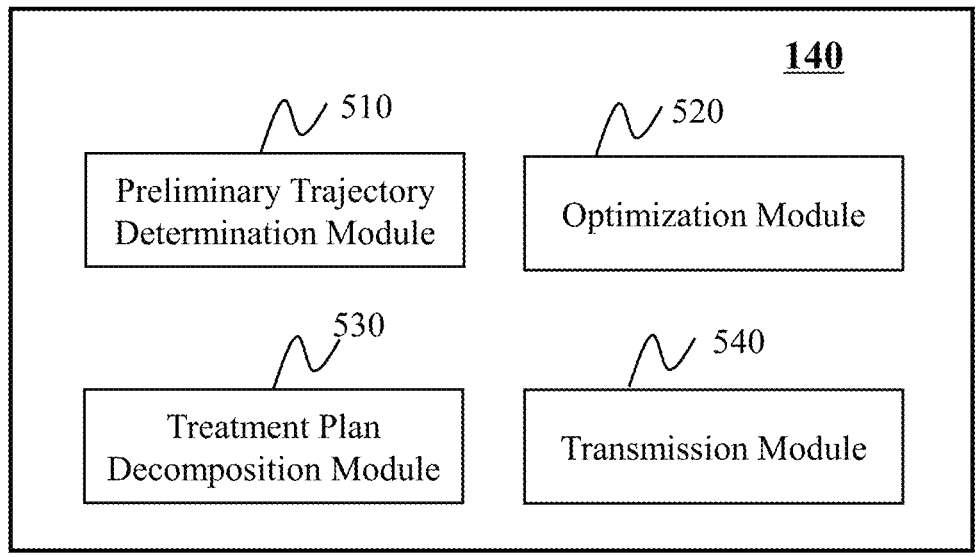
FIG. 5 is a block diagram illustrating an exemplary processing engine according to some embodiments of the present disclosure.

FIG. 5 is a block diagram illustrating an exemplary processing engine 140 according to some embodiments of the present disclosure. As illustrated in FIG. 5, the processing engine 140 may include a preliminary trajectory determination module 510, an optimization module 520, a treatment plan decomposition module 530, and a transmission module 540.

The preliminary trajectory determination module 510 may define a preliminary trajectory. The preliminary trajectory may include a plurality of control points. The control points may prescribe a number of parameters associated with the radiation delivery device 110 and how the values associated with the number of parameters change during the beam delivery. In some embodiments, the preliminary trajectory determination module 510 may determine the preliminary trajectory according to information associated with subject to be treated. Additionally or alternatively, at least part of the preliminary trajectory may be determined based on an input of a user (e.g., a doctor, a physicist). The input may include a desired value or range of a parameter related to the preliminary trajectory. In some embodiments, the preliminary trajectory determination module 510 may obtain a plurality of predetermined trajectories with respect to an organ to be treated, and select the preliminary trajectory from the predetermined trajectories. Details regarding the determination of the preliminary trajectory may be found elsewhere in the present disclosure (e.g., step 602 and the relevant descriptions thereof).

The optimization module 520 may optimize one or more parameters related to the preliminary trajectory. The parameter(s) to be optimized may include a collimator angle, an intensity, a MLC position, or the like, or any combination thereof. Additionally or alternatively, the optimization module 520 may generate a treatment plan based on the preliminary trajectory and the optimized parameter(s). In some embodiments, the optimization module 520 may optimize the parameter(s) according to an optimization technique, such as a fluence map optimization (FMO) technique, a direct aperture optimization (DAO) technique, or the like, or any combination thereof. Details regarding the optimization of the parameter(s) may be found elsewhere in the present disclosure (e.g., step 604 and the relevant descriptions thereof).

The treatment plan decomposition module 530 may decompose the treatment plan into a delivery trajectory including the plurality of control points. Each of the control points may be further associated with one or more optimized position parameters, output rate parameters and a plurality of motion parameters of a plurality of components of the radiation delivery device 110 (e.g., the gantry 220, the couch 230, the collimator 240, and the MLC leaves). The output rate may refer to radiations outputted by the radiation source 215 per unit time, generally represented by MU per minute. The motion parameters may be related to coordinated motions of the plurality of components of the radiation delivery device 110 during the beam delivery. In some embodiments, the decomposition of the treatment plan may be performed based on a plurality of constraints. The constraints may include a motion constraint related to a motion parameter, or the like, or any combination thereof. Details regarding the decomposition of the treatment plan may be found elsewhere in the present disclosure (e.g., step 606 and the relevant descriptions thereof).

The transmission module 540 may send information and/or instructions to one or more components of the RT system 100. In some embodiments, the transmission module 540 may send an instruction to direct the radiation delivery device 110 to deliver a treatment plan to the subject 250. For example, the instruction may include a variety of parameters related to the treatment plan, including the intensity (or optimized intensity if any), the output rate, the position parameters (or optimized position parameters if any), and motion parameters of multiple components of the radiation delivery device 110.

It should be noted that the above description regarding the processing engine 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more additional modules may be added, or one or more modules of the processing engine 140 may be combined into a single module. For example, the processing engine 140 may further include a collision detection module configured to detect collisions between the gantry 220, the subject 250, and/or the couch 230.

FIG. 6 is a flowchart illustrating an exemplary process for delivering a treatment plan to a subject according to some embodiments of the present disclosure. In some embodiments, one or more operations of process 600 illustrated in FIG. 6 may be implemented in the RT system 100 illustrated in FIG. 1. For example, at least a part of the process 600 illustrated in FIG. 6 may be stored in the storage device 150 in the form of instructions, and invoked and/or executed by the processing engine 140 (e.g., the processor 310 of the computing device 300 as illustrated in FIG. 3, the GPU 430 or CPU 440 of the mobile device 400 as illustrated in FIG. 4).

In 602, the preliminary trajectory determination module 510 may define a preliminary trajectory including a plurality of control points. A trajectory may refer to a travel path of a radiation source 215 around a subject 250. The control points may be arranged in a time order, and the radiation source 215 may travel though the positions defined by the control points in the time order according to the preliminary trajectory. The subject 250 may be a biological subject (e.g., a patient, an animal), or a non-biological subject (e.g., a phantom).

The plurality of control points may prescribe a number of parameters associated with the radiation delivery device 110 and how the values associated with the number of parameters change during the beam delivery. For example, each control point of the preliminary trajectory may include one or more position parameters of each of a plurality of components of the radiation delivery device 110. The plurality of components of the radiation delivery device 110 may include the gantry 220, the couch 230, the collimator 240, and the MLC leaves. In some embodiments, the position parameter of the gantry may include a gantry angle. The position parameter of the couch may include a couch position, or the like. The couch position may include the couch angle information. The position parameter of the collimator 240 may include a collimator angle. The position parameter of the MLC leaves may include a MLC leaf position. As used herein, the MLC leaf position may refer to a position of each individual leaf of the MLC.

In some embodiments, the preliminary trajectory determination module 510 may only initialize part of the one or more position parameters associated with the radiation delivery device 110 when the preliminary trajectory is defined. For example, the preliminary trajectory determination module 510 may only initialize the position parameter of the gantry 220 and the position parameter of the couch 230. The preliminary trajectory determination module 510 may define other parameters at a later stage based on the treatment requirements. Alternatively, the preliminary trajectory determination module 510 may initialize other parameters with default values and optimize those default values based on the treatment requirements. For example, the position parameter of the collimator 240 and/or the position parameter of the MLC leaves may further be optimized. In 602, the preliminary trajectory determination module 510 may define the preliminary trajectory by the gantry position parameter and the couch position parameter without defining the position parameters of the collimator 240 and/or the MLC leaves for each control point.

In some embodiments, the radiation type and/or radiation energy may be configured as a function of the position of the radiation source 215 along the preliminary trajectory. Exemplary radiation types may include electron beams, proton beams, neutron beams, photon beams, ion beams. Different types of radiations and/or different levels of radiation energy may be suitable for different portions (e.g., different organs or tissues) of the subject 250. For example, the electron beams may deliver a uniform dose from a surface of the subject 250 to a specific depth beneath the surface of the subject 250. The dose to be delivered after the specific depth of the surface of the subject 250 falls off rapidly, and thus sparing the deeper normal tissues from being radiated. As another example, the proton beams may be used to treat a specific target area without radiating any surrounding areas. An energy level may affect the penetrability of the radiation beams. For instance, the X-rays with a relatively low energy level (e.g., 16 keV-400 keV) may be used for a treatment of superficial tumors, while the X-rays with a relatively high energy level (e.g., 2 MeV or more) may be suitable for deep tumors. In some embodiments, when the radiation source 215 travels according to the preliminary trajectory, the radiation beams may irradiate different portions of the portions of the subject. The radiation type and/or radiation energy may need to be changed depending on the position of the radiation source 215 so that the irradiated portion may receive suitable type and/or level of radiations. Merely by way of example, during a treatment, the X-rays with the relatively low energy level may be used when the radiation beams irradiate the superficial tumors. When the radiation source 215 reaches a position for treating the deep tumors, the radiation type and/or energy may be changed. For instance, the X-rays with the relatively high energy level or the electron beams may be used to treat the deep tumors.

In some embodiments, the preliminary trajectory determination module 510 may automatically determine the preliminary trajectory by determining the plurality of control points. For example, the control points may be automatically determined based on the position, shape, and size of the ROI. Additionally or alternatively, at least part of the preliminary trajectory may be determined based on an input of a user (e.g., a doctor, a physicist). For example, a doctor may manually input a desired value or range of a parameter associated with one or more control points via a user interface of the terminal 130.

In some embodiments, the preliminary trajectory determination module 510 may obtain a plurality of predetermined trajectories with respect to an organ to be treated, and select the preliminary trajectory from the predetermined trajectories. The organ to be treated may be, for example, a breast, a brain, a stomach, a liver.

The predetermined trajectories may be obtained from a storage device in the RT system 100 (e.g., the storage device 150) or from an external source (e.g., a cloud platform) via the network 120. For example, the predetermined trajectories may be obtained from a library of predetermined trajectories suitable for various organs or tissues to be treated. The library of predetermined trajectories may include, for example, trajectories from historical treatment data. In some embodiments, the trajectories from historical patient treatment data may be classified into class solutions for clinical applications, such as the breast irradiation and the hippocampus-sparing total brain irradiation. In some embodiments, the library of predetermined trajectories may be generated based on the historical patient treatment data using a machine learning technique. The clinical information from the historical patient treatment data may be used as sample inputs of a machine learning model, and corresponding trajectories from historical patient treatment data may be used as sample outputs of the machine learning model. Exemplary clinical information related to a treatment may include a position, a size, and a shape of the ROI, the organs or tissues at risk surrounding the ROI, a stage of a malignant tumor, etc. The machine learning model may be used to generate the library of predetermined trajectories by classifying the trajectories from historical patient treatment data into the class solutions for clinical applications.

In some embodiments, the preliminary trajectory determination module 510 may select the preliminary trajectory among the plurality of predetermined trajectories based on clinical information of the subject 250. Additionally or alternatively, the selection of the preliminary trajectory may be performed based on an input of the user. The preliminary trajectory may be selected to minimize radiations to the normal organs or tissues surrounding the ROI. For example, the preliminary trajectory may be selected to minimize radiations to a heart, a chest cavity, a hippocampus, a temporal brain lobe, and/or a contralateral breast. As another example, when the organ to be treated is a breast, the preliminary trajectory may be selected to minimize radiations to a heart and a chest cavity.

In some embodiments, the preliminary trajectory determination module 510 may further perform a collision check to determine whether there may be a collision between the gantry 220 and the couch 230 or the subject 250. The collision check may be performed based on the spatial positions and the occupied space of the gantry 220, the couch 230, and the subject 250 defined by each control point. As used herein, the occupied space of a component may refer to the three-dimensional space occupied by the volume of the component (e.g., the gantry 220, the couch 230, or the subject 250). In some embodiments, the spatial position and the occupied space of each of the gantry 220, the couch 230, and the subject 250 may be illustrated as a set of points in a three-dimensional coordinate system. If an intersection is detected between different sets of points, there may be a possible collision between the gantry 220 and the couch 230 or the subject 250. If no intersection is detected between different sets of points, there may be no possible collision between the gantry 220 and either the couch 230 or the subject 250. If no possible collision is detected, the preliminary trajectory may be determined as suitable for radiation therapy. If a possible collision is detected, the preliminary trajectory may be determined as unsuitable, and the preliminary trajectory determination module 510 may amend the preliminary trajectory or determine another suitable preliminary trajectory.

In 604, the optimization module 520 may generate a treatment plan based on the preliminary trajectory by optimizing intensity, a position parameter of the collimator 240, and a position parameter of the MLC leaves for each control point. As described in connection with step 602, the position parameter of the collimator 240 may include a collimator angle and the position parameter of the MLC leaves may include a position of each individual leaf of the MLC. The intensity related to a control point may refer to a monitor unit value, representing the radiation output at that control point.

In some embodiments, the treatment plan may be determined to accomplish a treatment goal, for example, delivering a prescribed dose to the ROI, minimizing the radiations toward the normal organs or tissues surrounding the ROI, or maximizing the dose conformality. Predetermining the dose and one or more position parameters of the components of the radiation delivery device 110 may simplify the optimization at the cost of reducing the degrees of freedom and possibly restricting the treatment plan quality. It may be possible to design a treatment plan in which the dose and/or one or more position parameters are optimized to achieve a better treatment plan. For example, the collimator angle of each control point may be optimized so that the radiation beams may optimally accommodate to the ROI and decrease unnecessary radiation toward the surrounding organs or tissues (will be described in FIGS. 8A to 8B). As another example, the intensity and/or the MLC leaf position may also be optimized for each control point. The optimization of the intensity and the MLC leaf position may ensure that the field intensity and the field shape are modified to achieve the treatment goal.

In some embodiments, the optimization module 520 may optimize the collimator angle, the intensity, and the MLC leaf position according to an optimization technique. Exemplary optimization techniques may include a FMO technique, a DAO technique, or the like, or any combination thereof. For example, the optimization may be performed according to the FMO technique. The optimization module 520 may determine an optimized fluence map for each beam, and then decompose the optimized fluence maps into deliverable apertures (e.g., position parameters of the MLC leaves and/or the collimator 240) based on a leaf sequencing algorithm. In an optimized fluence map, a beam may be discretized into a plurality of beamlets, and the intensity of each beamlet may be individually controlled. As another example, the optimization may be performed according to the DAO technique. The DAO technique may directly determine the optimal collimator angle, the MLC leaf position, and/or the intensities of the beamlets. The DAO technique may incorporate a machine constraint of the MLC (e.g., the maximum number of MLC leaves), a distance constraint (e.g., the maximum distance to be travelled from one control point to the next control point) during the optimization process.

In some embodiments, the optimization module 520 may determine an objective function and one or more constraints related to the objective function, and then determine optimal parameters based on the objective function and the constraints via iterations. The objective function may include, for example, a biological objective function and a physical objective function. Exemplary constraints related to a biological objective function may include a tumor control probability (TCP), a normal tissue complication probability (NTCP), an equivalent uniform dose (EUD), machine constraints, or the like, or any combination thereof. The machine constraints may include a translation displacement constraint for the couch 230 and the MLC leaves, a rotation angle constraint for the gantry 220, the couch 230 and the collimator 240, etc. Exemplary constraints related to a physical objective function may include a dose distribution of the ROI, a tolerance dose of the surrounding organs or tissues, the machine constraints, or the like, or a combination thereof. The optimal parameters may be determined by an iterative algorithm, for example, a simulated annealing (SA) algorithm, a genetic algorithm (GA), a linear programming method, a gradient descent algorithm, or the like, or any combination thereof.

In some embodiments, the optimization of the collimator angle may be constrained in a limited range. The range may be determined by the optimization module 520 based on the clinical application and/or the organ to be treated, an input of the user, or a combination thereof. The ranges corresponding to different ROIs may be different according to different situations. For example, if the ROI has a relatively regular shape, a small range may be used to constrain the collimator angle; if the ROI has a relatively irregular shape, a large range may be used to constrain the collimator angle. Additionally or alternatively, the range may be determined by reference to the collimator angles in the library of predetermined trajectories.

The treatment plan may be determined based on the preliminary trajectory and the optimized parameter(s) related to the treatment. In some embodiments, a plurality of treatment plans may be determined and a suitable treatment plan may be selected, for example, manually by a user. Merely by way of example, a dose volume histogram (DVH) for each treatment plan may be displayed to the user via an interface of a terminal (e.g., the terminal 130). The DVH may exhibit a three-dimensional dose distribution at the ROI, the organs or tissues at risk, an isodose curve, etc. The user may then select the suitable treatment plan accordingly.

In 606, the treatment plan decomposition module 530 may decompose the treatment plan into a delivery trajectory including the plurality of control points. Each of the control points may be further associated with the optimized intensity, the optimized collimator angle, the optimized MLC leaf position, and a plurality of motion parameters. Each of the control points may be further associated with an output rate, which could be predefined as a constant value in some embodiments. In some other embodiments, the output rate related to each of the control points could serve as a constraint during optimization, and thus, the output rate may be variable. The output rate may refer to radiation outputted by the radiation source 215 per unit time. In some embodiments, the treatment plan decomposition module 530 may interpolate one or more sub-control points between two consecutive control points. Each sub-control point may be associated with the same kind of parameters as the control points.

The motion parameters may be related to coordinated motions of the plurality of components of the radiation delivery device 110 (e.g., the gantry 220, the couch 230, the collimator 240, and the MLC leaves). As described in connection with FIG. 2, an optimal multiplanar trajectory and a conformal radiation dose distribution may be achieved by coordinated motions of various components in the course of radiation treatment. The coordinated motions of various components may include a rotation, a translation motion, a pitch motion, and a roll motion of the couch 230, a rotation of the gantry 220, a rotation of the collimator 240, a motion of each leaf of the MLC, or the like, or any combination thereof. A motion of a component may include an accelerated motion, a uniform motion, a decelerated motion, or the like, or any combination thereof. In some embodiments, the gantry 220 and the couch 230 may rotate simultaneously with independently controlled speed during the treatment delivery according to the delivery trajectory. Additionally or alternatively, the couch motion may include at least one of a translation motion, a pitch motion, or a roll motion, and the motion of the couch 230 may be synchronous to the delivering of the treatment plan according to the delivery trajectory.

In some embodiments, a motion parameter of the gantry 220 or the collimator 240 may include a rotation direction, a rotation angle, a rotation speed, a rotation acceleration, or the like, or any combination thereof. A motion parameter of the couch 230 may include a roll direction, a roll angle, a translation direction, a translation displacement, a pitch direction, a pitch angle, a speed and an accelerated velocity of the roll motion, the translation motion, and/or the pitch motion, or the like, or any combination thereof. A motion parameter of the MLC leaves may include but not limited to a moving direction, a moving speed, an accelerated velocity of each individual MLC leaf.

In some embodiments, the decomposition of the treatment plan may be performed based on a plurality of constraints. The constraints may include an intensity constraint, a motion constraint related to a motion parameter, or the like, or any combination thereof. The intensity constraint herein could refer to the maximum number of pulses in a particular interval, maximum pulse repetition frequency (PRF), maximum radiation output rate or the like. For understanding of the intensity constraint and related modulation, U.S. patent application Ser. No. 15/690,363 entitled "SYSTEMS AND METHODS FOR PULSE PARAMETER MODULATION" could be referred to, the contents of which are hereby incorporated by reference. A motion constraint related to a motion parameter may include a maximum speed, a maximum acceleration, a maximum deceleration, a maximum displacement, a maximum rotation angle, or the like, or any combination thereof. The decomposed treatment plan may ensure that different components of the radiation delivery device 110, such as the gantry 220, the couch 230 may simultaneously reach a position defined by a control point under the constraints.

In some embodiments, the treatment plan decomposition module 530 may determine, for a segment of the treatment plan defined by two consecutive control points, a minimum duration for each component of the radiation delivery device 110 to traverse the segment. An optimized duration corresponding to the segment may be determined based on the minimum duration and a plurality of motion constraints associated with the components. Then the motion parameters for the components in the segment may be determined based on the optimized duration corresponding to the segment. Exemplary techniques for determining a delivery trajectory may be found in, for example, International Application No. PCT/CN2017/120051 filed Dec. 29, 2017, entitled "SYSTEM AND METHOD FOR SYNCHRONOUS MOTION OPTIMIZATION OF DEVICE WITH MOVING COMPONENTS," the contents of which are hereby incorporated by reference.

In some embodiments, the delivery trajectory determination module 530 may further perform a collision detection during the path from one control point to the next control point to ensure no collision occurs between the gantry 220 and the couch 230 or the subject 250. The collision detection may be performed based on motion parameters and spatial positions of the gantry 220, the couch 230, and the subject 250. If a collision is detected, the treatment plan decomposition module 530 may modify the path or replace the path by an alternative path without collision. For example, an additional control point may be inserted into the path to remove the collision, and the remaining path may be processed recursively in a similar manner.

In 608, the transmission module 540 may send an instruction to direct the radiation delivery device 110 to deliver the treatment plan to the subject 250.

The instruction may direct the radiation delivery device 110 to deliver radiation beams toward the ROI of the subject 250 in accordance with the treatment plan. For example, the instruction may include a variety of parameters related to the treatment plan, including the intensity (or optimized intensity if any), the output rate, the position parameters (or optimized position parameters if any), and motion parameters of multiple components of the radiation delivery device 110. After receiving the instruction, the control system of the radiation delivery device 110 may modulate the intensity delivery and synchronously adjust the movements of the plurality of components of the radiation delivery device 110 according to the instruction. In some embodiments, the subject 250 may receive the treatment in a prone position on the couch 230, for example, when the ROI is located in a breast or a brain.

Figure 7A:
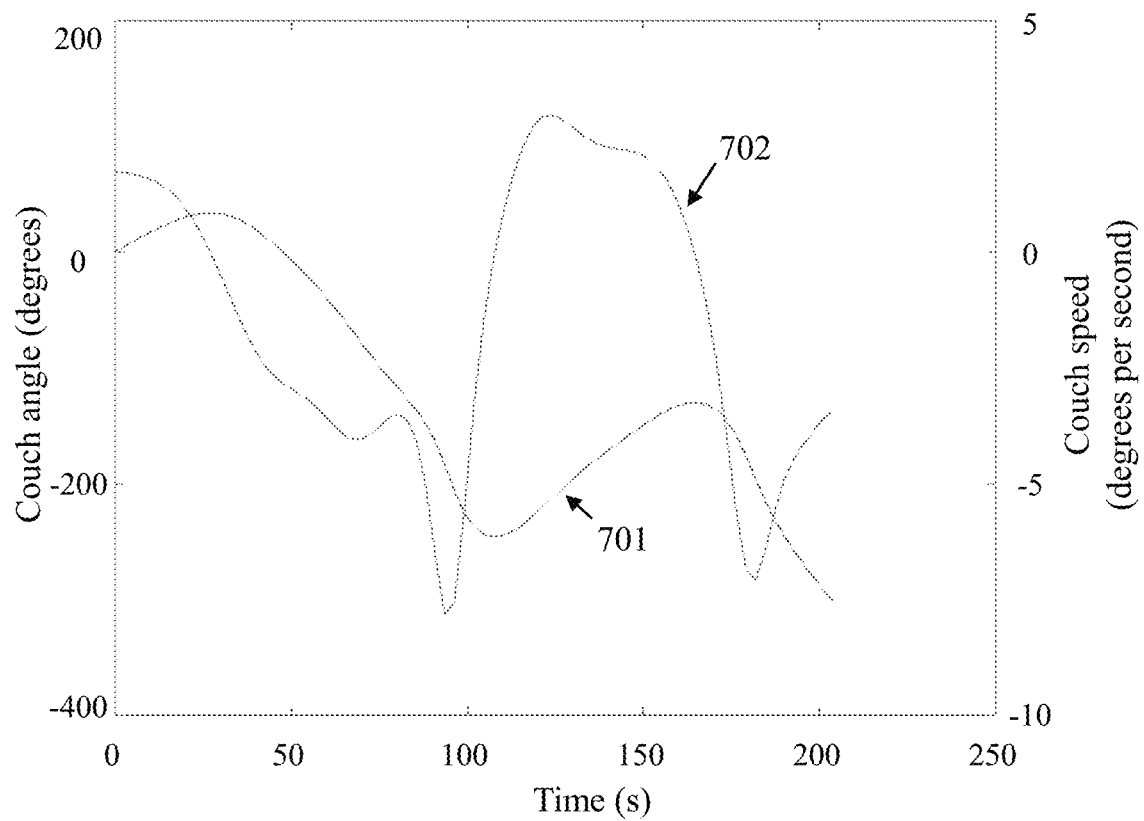
FIGS. 7A-7C are schematic diagrams illustrating exemplary motion parameters of a radiation delivery device as a function of time according to some embodiments of the present disclosure.
Figure 7B:
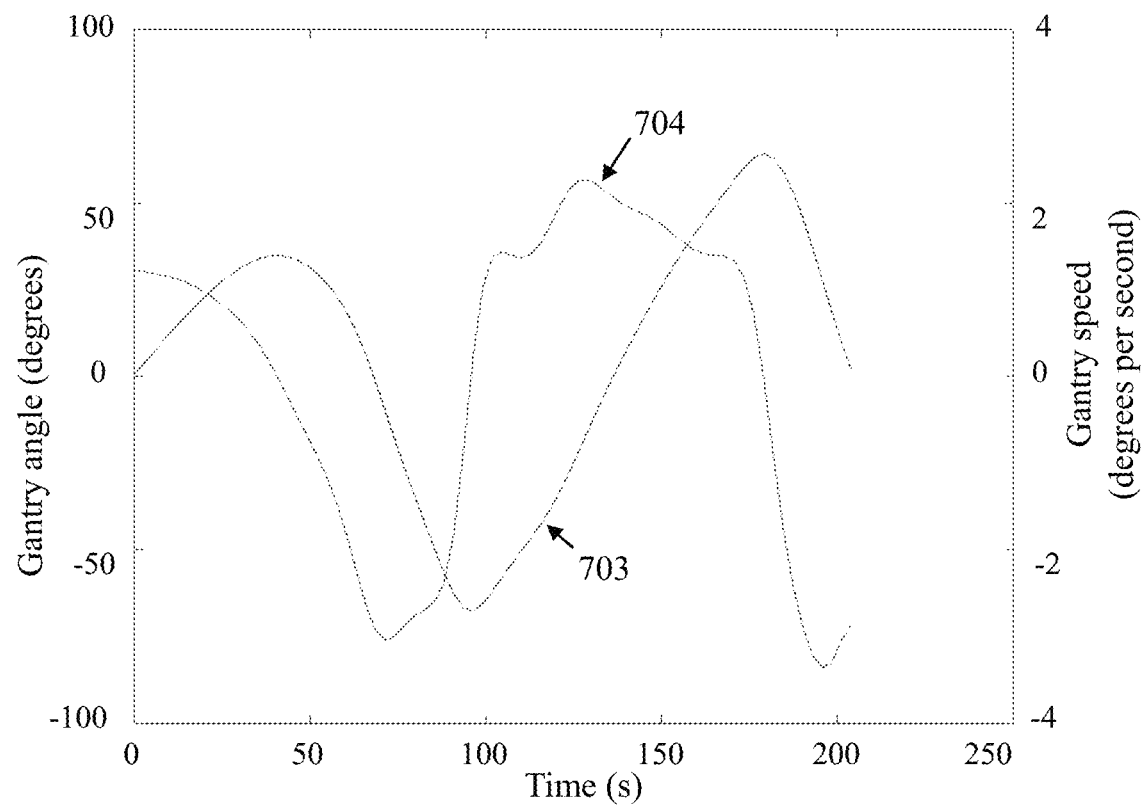
Figure 7C:
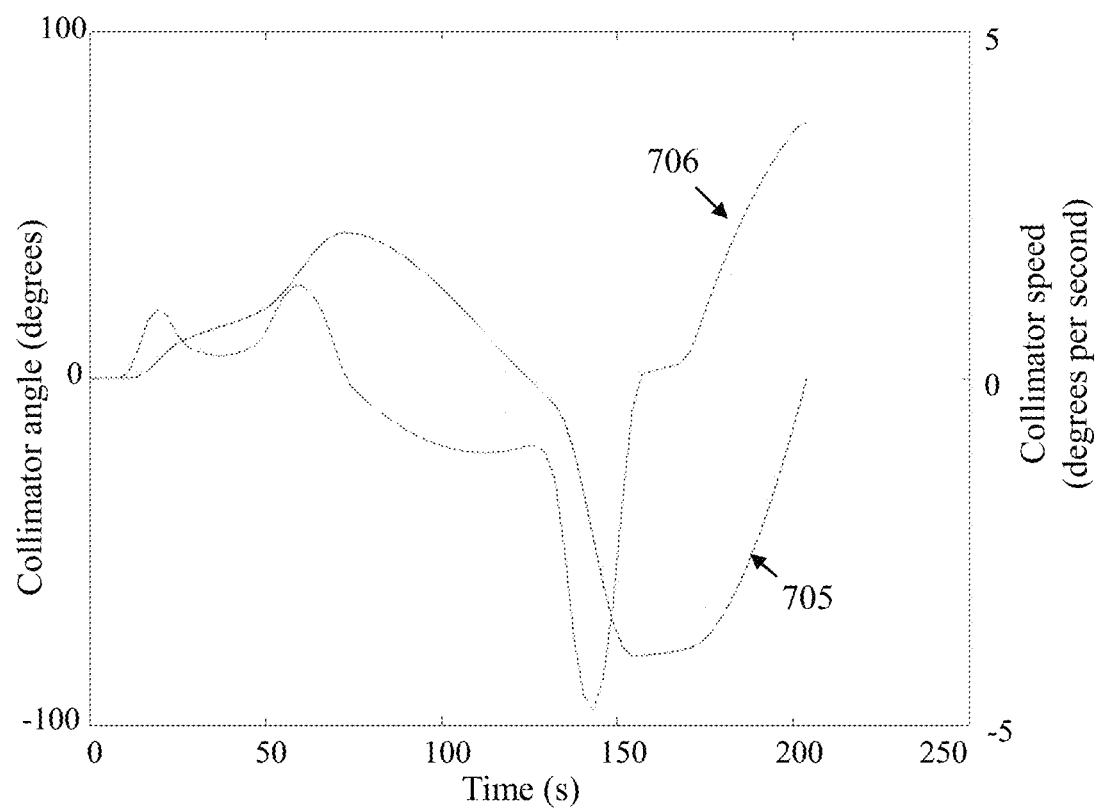

FIGS. 7A-7C are schematic diagrams illustrating exemplary motion parameters of a radiation delivery device 110 as a function of time according to some embodiments of the present disclosure. For illustration purposes, a clockwise direction may be defined as a positive direction and an anticlockwise direction may be defined as a negative direction, or the reverse.

FIG. 7A illustrates a change of a couch angle and a couch rotation speed during a couch rotation. A curve 701 and a curve 702 respectively represent the couch angle the couch speed during the couch rotation. FIG. 7B illustrates a change of a gantry angle and a gantry rotation speed during a gantry rotation. A curve 703 and a curve 704 respectively represent the gantry angle and the gantry rotation speed during the gantry rotation. FIG. 7C illustrates a change of a collimator angle and a collimator rotation speed during a collimator rotation. A curve 705 and a curve 706 respectively represent the collimator angle and the collimator rotation speed during the collimator rotation. As shown in FIGS. 7A to 7C, the couch 230, the gantry 220, and the collimator 240 may independently rotate at variable speeds, which may generate a multiplanar trajectory to better spare the healthy organs or tissues from receiving unnecessary radiation.

Figure 8A:
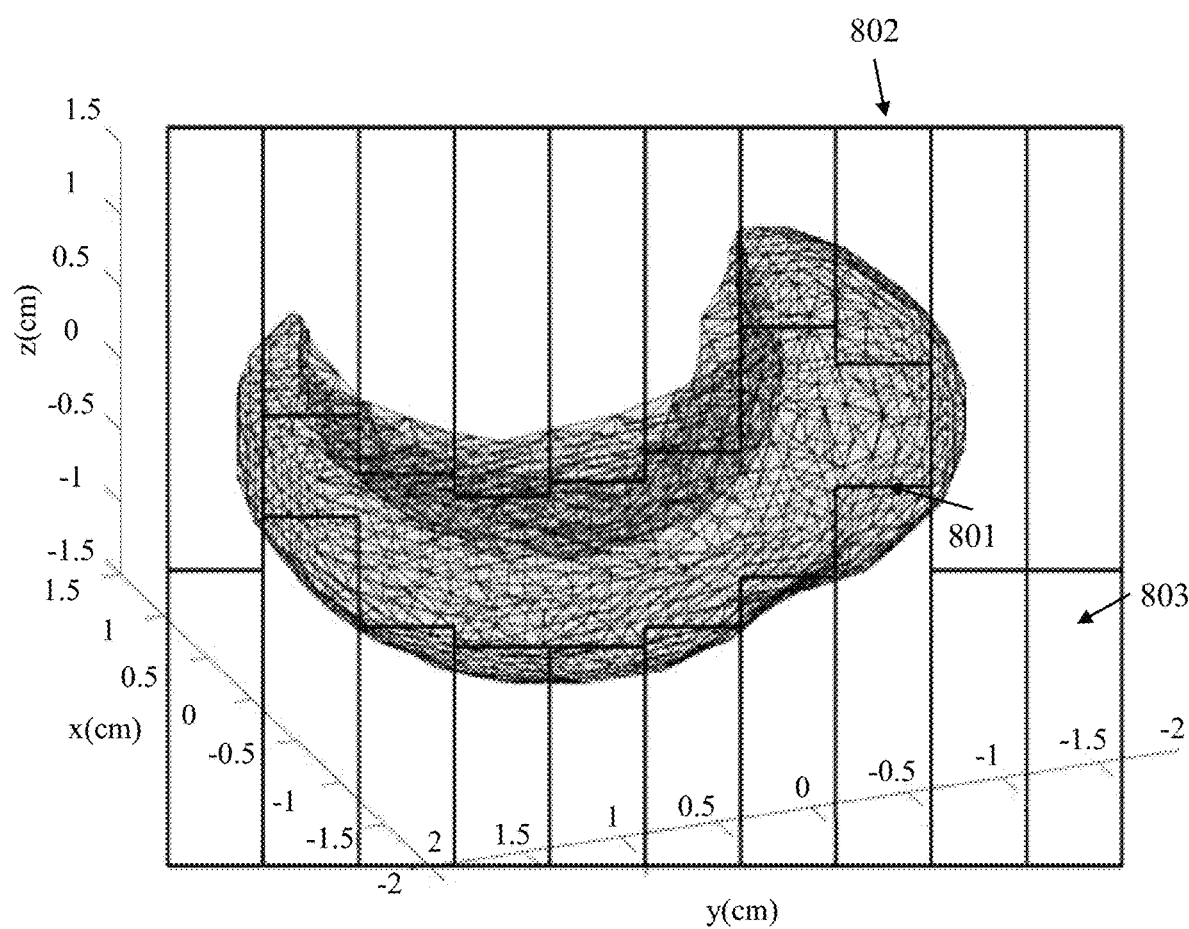
FIGS. 8A-8B are schematic diagrams illustrating beam's-eye-views for a target according to some embodiments of the present disclosure.
Figure 8B:
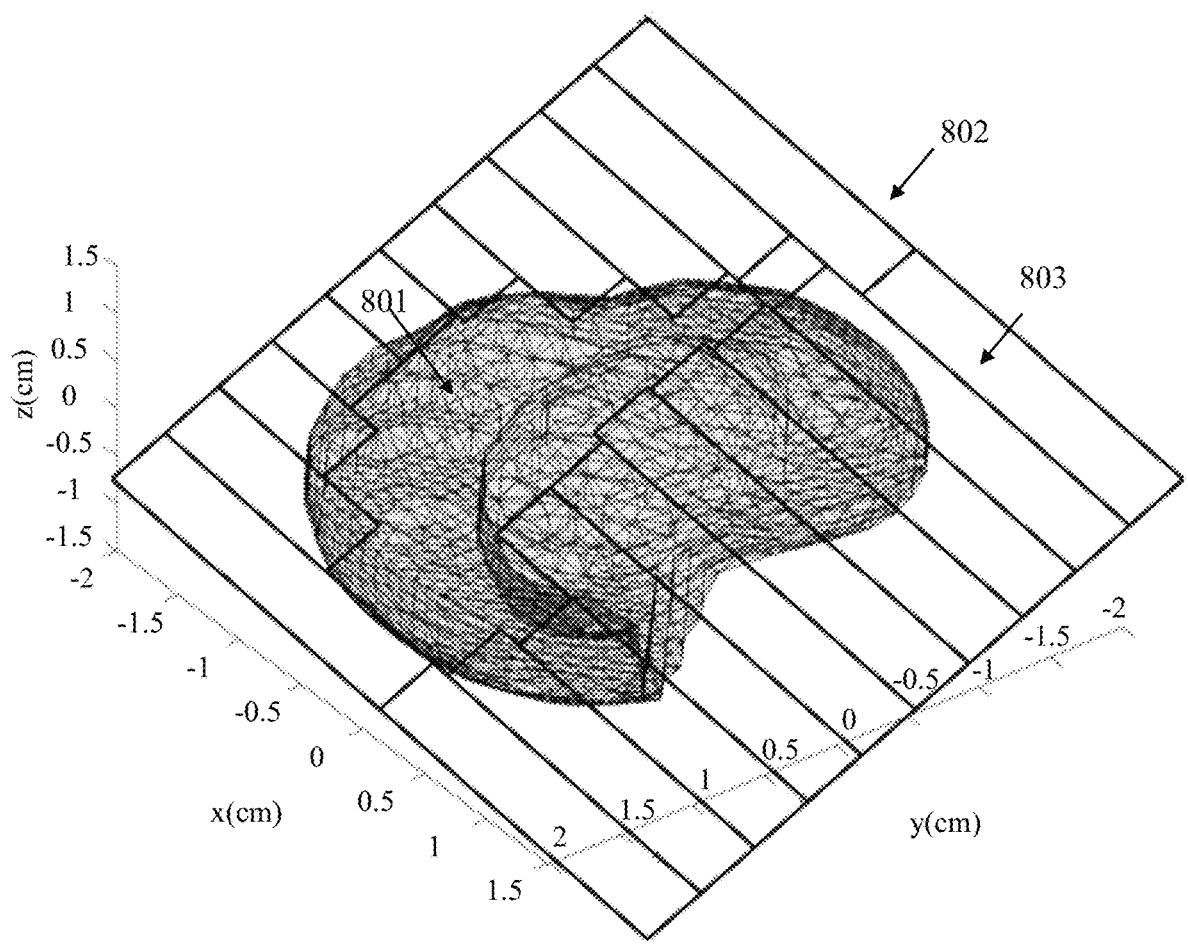

FIGS. 8A-8B are schematic diagrams illustrating beam's-eye-views for a target 801 according to some embodiments of the present disclosure. The target 801 may be an organ to be treated or a portion thereof. The target 801 may have a concavity in which there may be tissue that needs to be protected against radiation as illustrated in FIGS. 8A and 8B. For illustration purposes, a leaf pattern 802 is overlaid on the target 801. The radiation delivery device 110 may generate the leaf pattern 802 by adjusting the motions of the MLC leaves 803. When a beam angle changes as illustrated in FIG. 8A and FIG. 8B, it may be difficult to optimally accommodate the target 801 from a multiplanar arc trajectory if the collimator angle is not optimized at the same time, especially if the beam is to remain on while the collimator rotates. In addition to an optimization of the positions of the MLC leaves, an optimization of the collimator angle may facilitate the radiation beams to better conform to the shape of the target 801 in a more flexible manner.

It should be noted that the examples illustrated in FIGS. 7A-8B and the above descriptions thereof are merely provided for the purposes of illustration, and not intended to limit the scope of the present disclosure. For persons having ordinary skills in the art, multiple variations or modifications may be made under the teachings of the present disclosure. For example, the gantry 220, the couch 230, and/or the collimator 240 may rotate at any speed. However, those variations and modifications do not depart from the scope of the present disclosure.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A method for delivering radiation treatment to a subject using a radiation delivery device that includes a plurality of components, the plurality of components including one or more first components and one or more second components, the one or more first components including at least one of a collimator or multi-leaf collimator leaves, the one or more second components at least including a couch and a gantry, the method comprising:

defining a preliminary trajectory including a plurality of control points, the preliminary trajectory being defined by a position parameter of each second component for each control point without defining a position parameter of each first component for each control point, the position parameter of each second component for each control point is determined based on a position, a shape, and a size of a region of interest;

generating a treatment plan by optimizing, for each of the plurality of control points, the position parameter of each first component and an intensity;

decomposing the treatment plan into a delivery trajectory including the plurality of control points, each of the plurality of control points being further associated with the optimized intensity, the optimized position parameter of each first component, and a motion parameter of each second component; and instructing the radiation delivery device to deliver the treatment plan to the subject according to the delivery trajectory.

2. The method of claim 1, wherein the couch and the gantry are movable during the delivery of the treatment plan.

3. The method of claim 2, wherein the couch and the gantry move synchronously during the delivery of the treatment plan.

4. The method of claim 1, wherein the collimator and the gantry move synchronously during the delivery of the treatment plan.

5. The method of claim 1, wherein
the position parameter of the collimator includes a collimator angle, and
the optimization of the collimator angle is performed within a range determined based on at least one of clinical application or the region of interest.

6. The method of claim 5, wherein the range is determined based on a shape of the region of interest.

7. The method of claim 1, wherein the optimization of the position parameters of the one or more first components and the intensity is performed using at least one of a direct aperture optimization (DAO) technique or a fluence map optimization (FMO) technique.

8. The method of claim 1, further comprising:
performing a collision check on at least one of the preliminary trajectory or the delivery trajectory to avoid collision between the gantry and the subject or the couch during the delivery of the treatment plan to the subject.

9. The method of claim 1, wherein the defining the preliminary trajectory comprises:
obtaining a plurality of predetermined trajectories with respect to the region of interest; and
selecting the preliminary trajectory from the plurality of predetermined trajectories.

10. The method of claim 9, wherein the preliminary trajectory is selected to minimize radiation to at least one of a heart, a chest cavity, a hippocampus, a temporal brain lobe, or a contralateral breast of the subject.

11. The method of claim 9, wherein the plurality of predetermined trajectories are generated based on historical patient treatment data using a machine learning technique.

12. The method of claim 1, wherein the region of interest is at least one of a breast or a brain.

13. The method of claim 1, wherein the region of interest is a breast and the subject is treated in a prone position.

14. The method of claim 1, wherein the motion parameter of the couch is associated with at least one of a translation motion, a pitch motion, or a roll motion.

15. A system for delivering radiation treatment to a subject using a radiation delivery device that includes a plurality of components, the plurality of components including one or more first components and one or more second components, the one or more first components including at least one of a collimator or multi-leaf collimator leaves, the one or more second components at least including a couch and a gantry, the system comprising:
- at least one storage device storing a set of instructions; and
- at least one processor configured to communicate with the at least one storage device, wherein when executing the set of instructions, the at least one processor is configured to direct the system to perform operations including:
  - defining a preliminary trajectory including a plurality of control points, the preliminary trajectory being defined by a position parameter of each second component for each control point without defining a position parameter of each first component for each control point, the position parameter of each second component for each control point is determined based on a position, a shape, and a size of a region of interest;
  - generating a treatment plan by optimizing, for each of the plurality of control points, the position parameter of each first component and an intensity;
  - decomposing the treatment plan into a delivery trajectory including the plurality of control points, each of the plurality of control points being further associated with the optimized intensity, the optimized position parameter of each first component, and a motion parameter of each second component; and
  - instructing the radiation delivery device to deliver the treatment plan to the subject according to the delivery trajectory.

16. The system of claim 15, wherein the couch and the gantry are movable during the delivery of the treatment plan.

17. The system of claim 16, wherein the couch and the gantry move synchronously during the delivery of the treatment plan.

18. The system of claim 15, wherein the collimator and the gantry move synchronously during the delivery of the treatment plan.

19. The system of claim 15, wherein
- the position parameter of the collimator includes a collimator angle, and
- the optimization of the collimator angle is performed within a range determined based on at least one of clinical application or the region of interest.

20. A non-transitory computer readable medium, comprising a set of instructions for delivering radiation treatment to a subject using a radiation delivery device that includes a plurality of components, the plurality of components including one or more first components and one or more second components, the one or more first components including at least one of a collimator or multi-leaf collimator leaves, the one or more second components at least including a couch and a gantry, wherein when executed by at least one processor, the set of instructions direct the at least one processor to effectuate a method, the method comprising:
- defining a preliminary trajectory including a plurality of control points, the preliminary trajectory being defined by a position parameter of each second component for each control point without defining a position parameter of each first component for each control point, the position parameter of each second component for each control point is determined based on a position, a shape, and a size of a region of interest;
- generating a treatment plan by optimizing, for each of the plurality of control points, the position parameter of each first component and an intensity;
- decomposing the treatment plan into a delivery trajectory including the plurality of control points, each of the plurality of control points being further associated with the optimized intensity, the optimized position parameter of each first component, and a motion parameter of each second component; and
- instructing the radiation delivery device to deliver the treatment plan to the subject according to the delivery trajectory.

* * * * *